(12) United States Patent
Hadland

(10) Patent No.: US 8,705,693 B2
(45) Date of Patent: Apr. 22, 2014

(54) X-RAY INSPECTION SYSTEM AND METHOD

(75) Inventor: Roger Hadland, Tring (GB)

(73) Assignee: X-Tek Systems Limited, Tring (GB)

( * ) Notice: Subject to any disclaimer, the term of this patent is extended or adjusted under 35 U.S.C. 154(b) by 781 days.

(21) Appl. No.: 12/302,869

(22) PCT Filed: May 22, 2007

(86) PCT No.: PCT/GB2007/001896
§ 371 (c)(1),
(2), (4) Date: Nov. 28, 2008

(87) PCT Pub. No.: WO2007/138264
PCT Pub. Date: Dec. 6, 2007

(65) Prior Publication Data
US 2009/0268869 A1 Oct. 29, 2009

(30) Foreign Application Priority Data
May 27, 2006 (GB) .................................. 0610577.9

(51) Int. Cl.
*G01B 15/06* (2006.01)
(52) U.S. Cl.
USPC ............................................. 378/58; 378/21
(58) Field of Classification Search
USPC .............. 378/125, 137, 57, 58, 21, 25, 93, 94
See application file for complete search history.

(56) References Cited

U.S. PATENT DOCUMENTS

| | | | |
|---|---|---|---|
| 3,136,907 A * | 6/1964 | Kieffer et al. ................. | 378/144 |
| 4,748,650 A | 5/1988 | Ammann et al. | |
| 4,926,452 A | 5/1990 | Baker et al. | |
| 5,259,012 A | 11/1993 | Baker et al. | |
| 5,351,278 A | 9/1994 | Koshishiba et al. | |
| 5,594,770 A * | 1/1997 | Bowles et al. ................. | 378/58 |
| 6,339,635 B1 | 1/2002 | Schardt et al. | |
| 6,628,745 B1 * | 9/2003 | Annis et al. ..................... | 378/21 |

(Continued)

FOREIGN PATENT DOCUMENTS

WO   WO-2005/008716   1/2005

OTHER PUBLICATIONS

International Preliminary Report on Patentability from Application No. PCT/GB2007/001896.

(Continued)

*Primary Examiner* — Hoon Song
(74) *Attorney, Agent, or Firm* — Marshall, Gerstein & Borun LLP

(57) ABSTRACT

The invention provides an automatic system and method using x-ray inspection to image arrays of electrical interconnections on electronic devices. The electron beam of a rotating anode X-ray tube is deflected relative to the anode to cause emission of x-rays from different regions of the anode at different times. The x-ray tube is located at an inspection station for the electronic devices and disposed to irradiate a first part of the array of interconnections with x-rays emitted from a first region of the anode and to irradiate a further part of the array of interconnections with x-rays emitted from another region of the anode. X-rays emerging from the array of interconnections are detected and used to image part at least of the array in order to automatically register interconnection integrity failures and/or detect a performance trend in the formation of the connections. Typically, the arrays of electrical interconnections are established between a ball grid array on the underside of an electronics package and an array of blobs of solder paste on a printed circuit board.

26 Claims, 1 Drawing Sheet

(56) References Cited

U.S. PATENT DOCUMENTS

2004/0114712 A1    6/2004  Eppler et al.
2005/0105682 A1*   5/2005  Heumann et al. ............... 378/58
2008/0240344 A1*  10/2008  Reinhold ....................... 378/25

OTHER PUBLICATIONS

Written Opinion of the International Searching Authority from PCT/GB2007/001896.

* cited by examiner

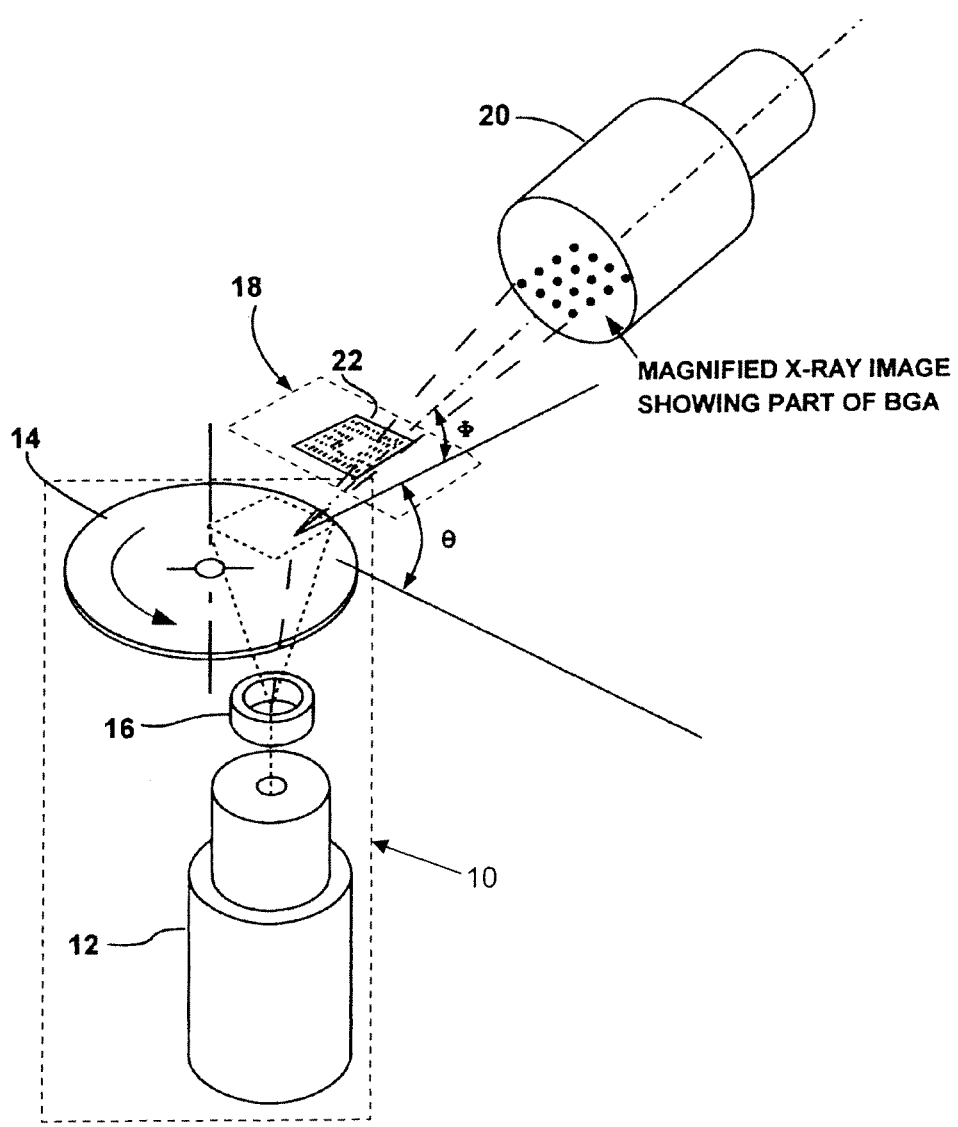

X-RAY INSPECTION SYSTEM AND METHOD

This invention relates to X-ray inspection systems and methods, and it relates more especially to such systems and methods for the automatic inspection of electronic components such as printed circuit boards ("PCBs").

PCBs are frequently mass-produced and sequentially presented at an inspection station for quality control inspection. In such circumstances, the rapid and reliable inspection of the PCBs to detect actual or incipient fault conditions is essential to the efficient running of the manufacturing plant, and difficult demands must be met if good quality control is to be maintained at commercially viable speeds.

Certain features of PCBs lend themselves to automatic optical inspection ("AOI"), which may typically be implemented by means of camera systems based on charge coupled device ("CCD") technology. Such AOI systems are used to check such things as correct orientation of components and the quality of visible solder joints, and to read component values, and all of these things can be done sufficiently rapidly as to present no real impediment to the desired working speed of the production plant.

On the other hand, there are certain features and components of PCBs, notably those that are not readily visible to an AOI system and, in particular, those relating to the quality of joints made between a PCB and the underside of an electronics package, for which AOI is not suitable and thus the quality control inspection process needs to be supplemented by an automatic X-ray inspection ("AXI") system. With the ever-increasing numbers of connections being provided between individual electronics packages, such as microprocessors and the like, and PCBs to which they are mounted, several techniques have been developed for making such connections rapidly and effectively. One example of such a technique is known as ball grid array ("BGA") technology in which connections brought out from the underside of an electronics package terminate in an array of individual, small conductive balls. Typically 400 or so such balls may be provided in a regular matrix array underneath an electronics package, and the surface of the PCB is prepared with a corresponding array of blobs of solder paste, deposited by means of a silk screen printing process, which act as terminals for a network of connections to selected locations and components on the PCB.

The electronics package is positioned on the PCB so that respective balls of the BGA array overlie respective solder paste blobs on the PCB and the assembly is then heated in an oven to fuse the solder, thereby forming a required array of connections between the electronics package and the PCB. At this point, it will be appreciated that the integrity and/or quality of the array of connections cannot be subjected to AOI, since the connections are formed directly beneath the electronics package. Thus AXI is typically utilised at this point.

It is to be noted that, depending upon the requirements of the quality control system, AXI may be used to detect connection failures and/or situations characteristic of incipient failure or, indeed merely of a general worsening of the standards of the connections, which may be controllable by feedback.

Even by means of AXI, however, difficulties arise in imaging the connection array with sufficient accuracy and speed for reliable quality control to be achieved at an acceptable rate which does not unduly slow the output of the production process, and it is an object of the invention to address such difficulties.

According to the invention from one aspect there is provided an automatic x-ray inspection system for producing images indicative of the integrity of electrical interconnections disposed in a predetermined array on an electronic device under inspection; the system comprising an x-ray tube having a rotating anode, a source of an electron beam directed at the anode, and deflecting means for moving the electron beam in relation to the anode so as to shift the beam from a first region on said anode to at least one further region thereof, thereby to cause the emission of x-radiation from said first and further regions at different times; the x-ray tube being located at an inspection station for said electronic device and disposed to irradiate a first part of said array of interconnections with x-radiation emitted from said first region of the anode and to irradiate a further part of said array of interconnections with x-radiation emitted from said at least one further region of said anode; the system further comprising detection means for detecting x-radiation emergent from said array of interconnections, means for imaging part at least of said array and means for automatically registering failures of integrity in said interconnections and/or for detecting a predetermined performance trend in the formation of said connections.

Preferably, the rotating anode of the x-ray tube comprises a transmission-type emissive target. This permits of a convenient source and detector arrangement in relation to the inspection station and the electronic devices presented thereto.

In preferred embodiments, the said electrical interconnections are established between a ball grid array on the underside of an electronics package and an array of blobs of solder paste on a PCB.

In some preferred embodiments, the deflecting means of the x-ray tube is configured such that the electron beam is sequentially shifted to a plurality of predetermined regions of the anode, said regions being so distributed over the anode as to ensure the sequential irradiation of respective portions of said array of electrical interconnections thereby, at the conclusion of the deflection sequence, to ensure the irradiation of the entire array of interconnections with x-radiation.

It will be appreciated that such a system irradiates the array of connections a portion at a time over the entire sequence; thereby facilitating the construction of an image of the connection integrity of the array on a block-by-block basis. This is a rapid and reliable procedure. Moreover, if desired and if necessary, such a "block-at-a-time" inspection system can be engineered to allow overlap between the edges of adjacent blocks, permitting the development of comparison signals capable of allowing for differences of x-ray emission from the various regions of the anode to which the electron beam is shifted.

According to the invention from another aspect there is provided a method of inspecting the integrity of electrical interconnections disposed in a predetermined array on an electronic device; the method comprising the steps of: providing an x-ray tube having a rotating anode and an electron beam directed toward the anode for impact thereon at a source location to generate a beam of x-radiation originating from said source location; deflecting the electron beam relative to the anode so as to shift the beam from a first source location on said anode to at least one further source location thereof, thereby to cause said beam of x-radiation to originate from said first and further locations at different times; disposing the x-ray tube to irradiate said electronic device at an inspection station for said electronic device and causing the x-ray tube to irradiate a first part of said array of interconnections with x-radiation emitted from said first source location and to irradiate a further part of said array of interconnections with x-radiation emitted from said at least one further source location; detecting x-radiation emergent from said array of interconnections; and imaging part at least of said array to automatically register failures of integrity in said interconnections and/or to detect a predetermined performance trend in the formation of said connections.

In some embodiments of the system or method of the invention, and wherein a worsening performance trend is detected, the system or method provides for the operation of a feedback procedure aimed at automatically controlling said trend.

The system or method of the invention preferably is configured for direct x-ray imaging, though it is also amenable to laminographic imaging.

In this context, it is well known that AXI can be implemented either by direct imaging or by laminography. Where laminography is used, it is typical for an X-ray spot and a detector to be scanned in respective, parallel circles and 180 degrees out of phase, describing a scanning pattern which can best be described as having the shape of an egg-timer. A plane of constant sharpness exists in the vicinity of the "waist" of the scanning pattern; its precise location and size depending at least in part on the radii of the two scanning circles. In any event, the "waist" is usually positioned at the interface which is to be inspected, such that everything before and after it in the x-ray path produces a smeared image. Software processing is used to extract the sharp image detail from the "waist" region of the scan and this detailed information is used to effect automatic evaluation of the integrity of the connections. However, existing systems have poor resolution and thus are difficult to program for automatic evaluation. As a result, they tend to exhibit unacceptably high false rejection rates. Such systems also tend to be extremely expensive, but they do not unduly slow down the production line.

As mentioned, above, it is preferred to use the present invention for direct imaging, and a system in accordance with one embodiment of the invention will now be described, by way of example only, with reference to the accompanying drawings, the single FIGURE of which shows, in schematic form, a perspective view of a system in accordance with an embodiment of the invention.

AXI systems employing direct imaging in a BGA context are configured to produce a sequence of high quality images of respective, restricted portions of the interconnection array. These portions are automatically analysed for porosity and the profile of the solder fillet to determine whether or not the solder has bonded at each connection point. Typically, with a BGA array comprising 400 balls, the sequential imaging of portions of the array, each amounting to (say) 4×4 balls, will require the sequential acquisition of data for the generation of 25 partial images, which significantly slows the production process. The use of larger portion sizes to reduce the data acquisition time leads to an increased false rejection rate and/or an increase in missed defects.

The prolonged data acquisition time associated with sequential imaging of partial images relating to portions of the overall array is at least in part attributable to the nature and mass of the x-ray tube. Conventional microfocus x-ray tubes have static targets and typically weigh between 15 and 40 kg. Speed is limited by the brightness of the x-ray source and the time taken to move the x-ray tube bodily from a position at which it irradiates one portion of the interconnection array to the position at which it irradiates the next portion of the array in the acquisition sequence to an accuracy of a few microns in space. To make this precise movement, and allow the tube to stabilise in its new position, typically requires 200 to 500 ms; a time which becomes significant when twenty-five or so views are needed for each complete BGA inspection.

In such conventional x-ray tubes, the electron beam power must be limited to about 1 watt per micron diameter in order to prevent the target (anode) surface from melting. A 10-micron spot thus operates at about 10 watts, at which level an exposure time of about a second is required in order to produce data with a signal-to-noise ratio adequate for the generation of images of sufficient quality for reliable automatic evaluation.

This embodiment of the present invention enables simultaneous increase in the x-ray output power and reduction in the data acquisition time, as will now be described with reference to FIG. 1, in which an x-ray tube, shown schematically at 10, comprises an electron beam source 12 of known kind, a rotating transmission target 14 and X-Y deflection coils 16, which may be electromagnetic or electrostatic. The system of FIG. 1 further includes an inspection station 18 and an x-ray detector arrangement 20. A BGA array 22 to be inspected by the system is disposed at the inspection station 18.

The rotating anode target 14 comprises a thin, x-ray transparent disc supporting a thin layer of target material, typically tungsten, deposited on its underside. This constitutes a so-called transmission target, since the x-rays emerge, in predictable directions characterized by angles $\theta$ and $\phi$, from the upper surface of the disc. Deflecting the electron beam to different regions of the target, whilst rotating the target at high speed, allows the power density and hence the brightness of the x-ray beam output from the x-ray tube 10 to be increased, typically in the order of fivefold to tenfold, without melting. This provides a directly proportional reduction in the data acquisition time without sacrifice in signal-to-noise ratio.

It is known per se, for example from EP-A-0030453, that deflection of the electron beam relative to a conventional rotating anode x-ray tube target can reduce the effects of localised heating. However, in the present embodiment, the deflection is effected in accordance with a sequential and pre-ordered shifting pattern that enables the various twenty-five or so portions of the BGA array to be sequentially irradiated without the need for any physical movement of the x-ray tube 10. Deflection from point to point of the predetermined shifting pattern is substantially instantaneous and moreover no stabilisation time is required.

Thus, in this preferred embodiment of the invention, the deflection coils 16 of the x-ray tube 10 are configured and fed with deflecting waveforms such that the electron beam generated by the source 12 is sequentially shifted to a plurality of predetermined regions of the rotating anode 14; the regions being so distributed over the anode as to ensure the sequential irradiation of respective portions of the entire array of BGA connections with the PCB thereby, at the conclusion of the deflection sequence, to ensure the irradiation of the entire array of interconnections with x-radiation.

Such a system thus irradiates the array of connections, a portion at a time, over the entire sequence; thereby facilitating the construction of an image of the connection integrity of the array on a block-by-block basis, providing a rapid and reliable procedure.

As previously mentioned, if there is any likelihood of a variation in the x-ray beam output from the various locations of the target over which the electron beam is scanned, the portion of the array irradiated from one target location may be arranged to slightly overlap the portion of the array irradiated from another target location, thereby to permit duplication of limited amounts of data for comparison and calibration purposes.

It will be appreciated that, although the specific embodiment of the invention has been described for use with BGA technology (including so-called micro-BGA), the invention is not limited to such technology, and may be used with any technique used to connect electronic components to PCBs. Examples of alternative technologies to BGA are those based on the use of land grid arrays, pin grid arrays, flip-chips, multi-chip modules, printed through-holes and indeed any soldered joints hidden from view, such as under connector assemblies.

It will also be appreciated that the invention may be used in quality control systems aimed at detecting actual connection failures and/or in systems configured to detect conditions which indicate a performance trend which, if continued, could lead to connection failures. Systems of the first kind tend to indicate PCBs on which connections of unacceptable quality have been detected, whereas systems of the second kind can be incorporated into a feedback loop aimed at correcting the performance trend before it leads to actual connection failures. Such automated feedback systems are commonly referred to as employing statistical process control.

In order to utilise the system of the invention for laminography, the deflection coils 16 are arranged to deflect the electron beam along a circular or other path on the rotating anode target 14, in synchrony with motion of a detector system.

I claim:

1. An x-ray inspection system for producing images of a device under inspection, the system comprising;
   an x-ray tube having a rotating anode;
   a source of an electron beam directed at the anode; and
   a deflector for moving the electron beam in relation to the anode so as to shift the beam from a first region on said anode to at least one further region thereof, to cause the emission of x-radiation from said first and further regions at different times, the x-ray tube being located at an inspection station for said device and disposed to irradiate a first part of said device with x-radiation emitted from said first region of the anode and to irradiate a further part of said device with x-radiation emitted from said at least one further region of said anode; and
   a detector comprising an x-ray visualization surface for detecting x-radiation emergent from said device,
   wherein the x-ray visualization surface, the device and the x-ray tube are held in fixed relative spatial relation during inspection.

2. The system according to claim 1, wherein the anode of the x-ray tube comprises a transmission-type emissive target.

3. The system according to claim 2, wherein an array of electrical interconnections are established between a ball grid array on the underside of an electronics package and an array of blobs of solder paste on a printed circuit board of the electronics package.

4. The system according to claim 1, wherein the deflector of the x-ray tube is configured such that the electron beam is sequentially shifted to a plurality of predetermined regions of the anode, said regions being so distributed over the anode as to ensure the sequential irradiation of respective portions of said device thereby, at the conclusion of the deflection sequence, to ensure the irradiation of the entire array of interconnections with x-radiation.

5. The system according to claim 1, wherein the deflector of the x-ray tube is configured such that the electron beam is sequentially shifted to a plurality of predetermined regions of the anode, said regions being so distributed over the anode as to ensure the sequential irradiation of respective portions of said device thereby, at the conclusion of the deflection sequence, to ensure the irradiation of the entire array of interconnections with x-radiation, and
   wherein the portion of the array irradiated from one region of said anode overlaps, at least partially, the portion of the array irradiated from another region of said anode, to permit duplication of limited amounts of data for comparison and calibration purposes.

6. The system according to claim 4, wherein a predetermined performance trend is indicative of a worsening quality of said connections and wherein a feedback system is provided to develop a feedback signal to arrest or reverse said trend.

7. A direct x-ray imaging arrangement including a system according to claim 1.

8. A laminographic imaging arrangement including a system according to claim 1.

9. A method of inspecting a device, the method comprising:
   providing an x-ray tube having a rotating anode and an electron beam directed toward the anode for impact thereon at a source location to generate a beam of x-radiation originating from said source location;
   deflecting the electron beam relative to the anode so as to shift the beam from a first source location on said anode to at least one further source location thereof, to cause said beam of x-radiation to originate from said first and further locations at different times;
   disposing the x-ray tube to irradiate said device at an inspection station for said device and causing the x-ray tube to irradiate a first part of said device with x-radiation emitted from said first source location and to irradiate a further part of said device with x-radiation emitted from said at least one further source location; and
   detecting, using an x-ray visualization surface of a detector, x-radiation emergent from said device,
   wherein the x-ray visualization surface, the device and the x-ray tube are held in fixed relative spatial relation during inspection.

10. The method according to claim 9 comprising developing a feedback signal for use in arresting or correcting a performance trend, when the predetermined performance trend is indicative of a worsening quality of said connections.

11. The method according to claim 9, wherein the device is an electronic device comprising electrical interconnections disposed in a predetermined array.

12. The method according to claim 11, further comprising imaging at least a part of said array to automatically register failures of integrity in said interconnections and/or to detect a predetermined performance trend in the formation of said connections.

13. The method according to claim 9, wherein inspection is automatic.

14. The system according to claim 1, wherein the device is an electronic device comprising electrical interconnections disposed in a predetermined array.

15. The system according to claim 1, wherein the device is an electronic device comprising electrical interconnections disposed in a predetermined array, the system further comprising an imager for imaging at least a part of said array and an automatic registering system for automatically registering failures of integrity in said interconnections and/or for detecting a predetermined performance trend in the formation of said connections.

16. The system according to claim 1 wherein inspection is automatic.

17. An automatic x-ray inspection system for producing images indicative of the integrity of electrical interconnections disposed in a predetermined array on an electronic device under inspection, the system comprising:
- an x-ray tube having a rotating anode;
- a source of an electron beam directed at the anode;
- a deflector for moving the electron beam in relation to the anode so as to shift the beam from a first region on said anode to at least one further region thereof, to cause the emission of x-radiation from said first and further regions at different times, the x-ray tube being located at an inspection station for said electronic device and disposed to irradiate a first part of said array of interconnections with x-radiation emitted from said first region of the anode and to irradiate a further part of said array of interconnections with x-radiation emitted from said at least one further region of said anode;
- a detector comprising an x-ray visualization surface for detecting x-radiation emergent from said array of interconnections;
- an imager for imaging at least part of said array; and
- an automatic registration system for automatically registering failures of integrity in said interconnections and/or for detecting a predetermined performance trend in the formation of said connections,
- wherein the x-ray visualization surface, the device and the x-ray tube are held in fixed relative spatial relation during inspection.

18. The system according to claim 17, wherein the anode of the x-ray tube comprises a transmission-type emissive target.

19. The system according to claim 17, wherein said electrical interconnections are established between a ball grid array on the underside of an electronics package and an array of blobs of solder paste on a printed circuit board of the electronics device.

20. The system according to claim 17, wherein the deflector of the x-ray tube is configured such that the electron beam is sequentially shifted to a plurality of predetermined regions of the anode, said regions being so distributed over the anode as to ensure the sequential irradiation of respective portions of said device thereby, at the conclusion of the deflection sequence, to ensure the irradiation of the entire array of interconnections with x-radiation.

21. The system according to claim 17, wherein the deflector of the x-ray tube is configured such that the electron beam is sequentially shifted to a plurality of predetermined regions of the anode, said regions being so distributed over the anode as to ensure the sequential irradiation of respective portions of said device thereby, at the conclusion of the deflection sequence, to ensure the irradiation of the entire array of interconnections with x-radiation, and
- wherein the portion of the array irradiated from one region of said anode overlaps, at least partially, the portion of the array irradiated from another region of said anode, to permit duplication of limited amounts of data for comparison and calibration purposes.

22. The system according to claim 17, wherein said predetermined performance trend is indicative of a worsening quality of said connections and a feedback system is provided to develop a feedback signal to arrest or reverse said trend.

23. A direct x-ray imaging arrangement including a system according to claim 17.

24. A laminographic imaging arrangement including a system according to claim 17.

25. A method of inspecting the integrity of electrical interconnections disposed in a predetermined array on an electronic device, the method comprising:
- providing an x-ray tube having a rotating anode and an electron beam directed toward the anode for impact thereon at a source location to generate a beam of x-radiation originating from said source location;
- deflecting the electron beam relative to the anode so as to shift the beam from a first source location on said anode to at least one further source location thereof, to cause said beam of x-radiation to originate from said first and further locations at different times;
- disposing the x-ray tube to irradiate said electronic device at an inspection station for said electronic device and causing the x-ray tube to irradiate a first part of said array of interconnections with x-radiation emitted from said first source location and to irradiate a further part of said array of interconnections with x-radiation emitted from said at least one further source location;
- detecting, using an x-ray visualization surface of a detector, x-radiation emergent from said array of interconnections; and
- imaging at least part of said array to automatically register failures of integrity in said interconnections and/or to detect a predetermined performance trend in the formation of said connections,
- wherein the x-ray visualization surface, the device and the x-ray tube are held in fixed relative spatial relation during inspection.

26. Method according to claim 10 or 25 comprising developing a feedback signal for use in arresting or correcting said trend.

* * * * *